United States Patent [19]
Bünning et al.

[11] Patent Number: 5,658,552
[45] Date of Patent: Aug. 19, 1997

[54] HAIR SPRAY COMPOSITION CONTAINING A WATER-DISPERSIBLE SILICONE WAX

[75] Inventors: Einhard Bünning, Seeheim-Jugenheim; Christine Cajan, Bad Ems, both of German Dem. Rep.

[73] Assignee: Goldwell GmbH, Germany

[21] Appl. No.: 450,543

[22] Filed: May 25, 1995

[30] Foreign Application Priority Data

Jun. 20, 1994 [DE] Germany .................. 44 21 562.2

[51] Int. Cl.$^6$ .................................. A61K 7/11
[52] U.S. Cl. .................. 424/45; 424/47; 424/DIG. 1; 424/DIG. 2; 424/70.11; 424/70.12; 514/957
[58] Field of Search .............. 424/45, 47, DIG. 1, 424/DIG. 2, 70.12, 70.11; 514/957

[56] References Cited

U.S. PATENT DOCUMENTS

| | | | |
|---|---|---|---|
| 4,300,580 | 11/1981 | O'Neill et al. | 424/DIG. 2 |
| 4,834,968 | 5/1989 | Bolich, Jr. | 424/45 |
| 4,839,167 | 6/1989 | Yamamoto et al. | 424/45 |
| 5,126,126 | 6/1992 | Varaprath et al. | 424/47 |
| 5,158,762 | 10/1992 | Pierce | 424/47 |
| 5,176,898 | 1/1993 | Goldberg et al. | 424/70.11 |

FOREIGN PATENT DOCUMENTS

| | | |
|---|---|---|
| 0205306 | 12/1986 | European Pat. Off. . |
| 0431219 | 6/1991 | European Pat. Off. . |
| 0551748 | 7/1993 | European Pat. Off. . |
| 0557087 | 8/1993 | European Pat. Off. . |
| 9000045 | 1/1990 | WIPO . |
| 9303703 | 3/1993 | WIPO . |

OTHER PUBLICATIONS

Martino, G.T., et al. (1992). Spray Technology & Marketing, Mar. Issue, pp. 34–39.
Johnson, M.A. et al. (1992). Spray Technology & Marketing, Jun. Issue, pp. 32–39.

*Primary Examiner*—Raj Bawa
*Attorney, Agent, or Firm*—Londa and Traub LLP

[57] ABSTRACT

The invention refers to a hair spray containing a low proportion of volatile compounds and having improved spraying and setting properties comprising a) about 5% to about 50% of at least one lower alcohol selected from the group of ethanol, n-propanol and (or) isopropyl alcohol;

b) about 15% to about 70% by wt. water;

c) about 1% to about 15% by wt. of at least one film-forming polymer;

d) about 0.1% to about 3% by wt. of a water-dispersible silicone wax of the general formula I, $$CH_3-(OCH_2CH_2)_n-O-\underset{\underset{CH_3}{|}}{\overset{\overset{CH_3}{|}}{Si}}-O-(CH_2CH_2O)_m-CH_3, \quad (I)$$

wherein n and m may be identical or different and denote an integer between 10 and 20; which is either packed e1) as an aerosol spray composition with dimethyl ether or a compressed gas selected from the group of di-nitrogen oxide, air, nitrogen and (or) carbon dioxide as propellent, or e2) as a manually operated pump spray.

8 Claims, No Drawings

HAIR SPRAY COMPOSITION CONTAINING A WATER-DISPERSIBLE SILICONE WAX

BACKGROUND OF THE INVENTION

1. Field of the Invention

This invention comprises a hair spray providing improved properties of use but having a low amount of volatile compounds.

2. Description of the Prior Art

Hair sprays with a low content of volatile organic compounds (known as 'VOC' among experts) have become popular for ecological reasons just recently.

Typical compositions of this type are, e.g., described in U.S. Pat. No. 5,176,898 to Goldberg.

The most common substitute for these volatile compounds is water for reasons of costs and environment.

However, as practice has proved, this option is limited because the spray pattern—when being discharged from the can—distinctly shows formation of droplets which, after evaporation of the liquid ingredients, leave pearly resinous residues of the film-forming agent on the dry hair, and thus do not provide a homogeneous film thereon.

SUMMARY OF THE INVENTION

The present invention overcomes these disadvantages by providing a hair spray with a low proportion of volatile compounds but having an improved spraying performance without the formation of droplets and thus allowing a uniform distribution of the film-forming agent on the hair with reduced drying time.

The hair spray of the invention comprises a) about 5% to about 50%, preferably 15% to 40% by wt. of at least one lower alcohol selected from the group of ethanol, n-propanol, and (or) isopropyl alcohol;

b) about 15% to about 70%, preferably about 20% to about 50% by wt. water;

c) about 1% to about 15%, preferably about 2.5% to about 10% by wt. of at least one film-forming polymer; and d) about 0.1% to about 3%, preferably about 0.5% to about 1.5% by wt. of a water-dispersible silicone-wax of the general formula I:

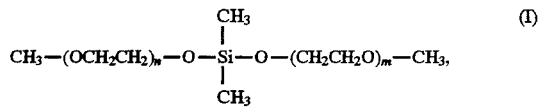

wherein n and m may be identical or different denoting an integer from 10 to 20, preferably between 14 and 18, whereby the composition may be packaged either as a manually operated pump-spray composition or as an aerosol spray with dimethyl ether as propellent or a compressed gas of the group of dinitrogen oxide, nitrogen, air and (or) carbon dioxide.

The preferred proportion of dimethyl ether in aerosol sprays is between about 10% and about 40%, particularly about 20% to about 30% by wt. of the total composition.

Part of dimethyl ether may be substituted by propane, butane and (or) isobutane which, e.g., can make up to about 30% of the total propellant mixture.

If compressed gases are used, their quantity is selected so that the aerosol composition has a pressure of about 5 to about 15, preferably 6 to 14, particularly 8 to 12 bar.

For further improvement of the spraying pattern, alkanes with 5 to 9 carbon atoms may be added as solubilizers.

Those are in particular n-pentane, iso-pentane, n-hexane, iso-hexane, n-heptane, iso-heptane, n-octane, iso-octane and (or) n-nonane.

The addition of these alkanes to aerosol sprays is already known from WO-A 91/08730 and 93/18735; the optimal quantity is from about 5% to about 25% by wt. of the total composition.

It is believed that the addition of the water-dispersible silicone wax as defined in general formula I (above) improves the dispersing activity of the total preparation and therefore effects improved spraying and film-forming properties of the product.

This effect may still be improved if the above defined silicone wax is used in admixture with a polyethylene glycol dimethyl ether having about the same number of ethylene oxide groups in a proportion of about 75:25 to 90:10, preferably about 80:20 to about 85:15.

A corresponding product, e.g., is on the market under the name "DOW CORNING® 2501 COSMETIC WAX" and is mainly recommended for use as moisturizing agent.

Basically any polymers suggested and known for this purpose are suitable as film-forming polymers.

Suitable anionic polymers are particularly the known crotonic acid and acrylic acid copolymers, e.g. vinyl acetate/crotonic acid/or vinyl acetate/vinyl neodecanoate/crotonic acid copolymers of the type "Resyn®"; sodium acrylate/vinyl alcohol copolymers of the type "Hydagen® F"; sodium polystyrol sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers; acrylic acid/acrylamide copolymers or sodium salts thereof of the type "Reten®", etc.

Other suitable anionic polymers are vinyl alkyl ether, particularly methyl vinyl ether/maleic acid copolymers prepared by hydrolysis of vinyl ether/maleic acid anhydride copolymers and sold under the trade names "Gantrez® AN or ES". These polymers may also be partially esterified, e.g. "Gantrez® ES 225", the ethyl ester of an ethyl vinyl ether/maleic acid copolymer or the butyl or isobutyl ester thereof.

Suitable nonionic polymers used in the hair sprays according to the invention alone or preferably in admixture with anionic and (or) amphoteric or zwitterionic polymers are particularly vinyl pyrrolidone homo- or copolymers, e.g., of the type "Luviskol®".

These are polyvinyl pyrrolidone or copolymers of vinyl pyrrolidone and vinyl acetate, as well as terpolymers of vinyl pyrrolidone, vinyl acetate, and other vinyl esters, such as vinyl propionate.

Further copolymers are those prepared from vinyl pyrrolidone and dimethyl aminoethyl methacrylate (Copolymers 845, 937 or 958 of GAF Co.), and terpolymers of vinyl caprolactame, vinyl pyrrolidone and dimethyl aminoethyl methacrylate (Copolymer VC-713 of GAF Co.).

Film-forming agents of natural origin, such as chitosane and the derivatives thereof, may also be used, particularly in admixture with synthetic polymers.

Amphoteric polymers used either alternatively to or in admixture with anionic and (or) nonionic polymers are particularly copolymers of N-octyl acrylamide, (meth) acrylic acid and tert. butyl aminoethyl methacrylate of the type "Amphomer®"; copolymers of methacryloyl ethyl betaine and alkyl methacrylates of the type "Yukaformer®", e.g., butyl methacrylate copolymer "Yukaformer® Am75"; copolymers of monomers containing carboxylic groups or sulfonic groups, e.g., (meth)acrylic acid and itaconic acid containing basic, especially amino group monomers, such as mono- or dialkyl aminoalkyl (meth)acrylates or mono- or dialkyl aminoalkyl (meth)acrylamides; copolymers of N-octyl acrylamide, methyl methacrylate, hydroxypropyl methacrylate, N-tert.-butyl aminoethyl methacrylate and acrylic acid as well as the copolymers disclosed in U.S. Pat. No. 3,927,199.

As with anionic polymers, all amphoteric polymers normally used in hair products may naturally also be used.

The anionic, nonionic and amphoteric polymers may also be used in admixture, as already mentioned.

For this purpose, mixtures of the trade product "Amphomer®", which is a copolymer of N-octyl acrylamide, acrylic acid and tert.-butyl aminoethyl methacrylate, on the one hand, and vinyl acetate/crotonic acid polymers of the type "Resyn®", on the other hand have been particularly successful, but as already mentioned, the use of mixtures of any one or more of the above listed anionic, nonionic and amphoteric polymers is generally possible.

The compositions according to the invention may comprise the conventional additives in hair sprays, e.g., further solubilizers such as lower polyalcohols and the toxicologically compatible ethers and esters thereof, emollients, high and less volatile silicones, neutralizers for carboxylic groups containing film-forming agents, antistatic agents, ultraviolet absorbants, perfumes, etc., as they are are known by the state of the art.

DESCRIPTION OF THE PREFERRED EMBODIMENTS

The following examples illustrate the invention in detail.

EXAMPLE 1

| | |
|---|---|
| Ethanol | 34.7 (% by wt.) |
| Acrylic acid/ethyl acrylate/N-tert.-butyl acrylamide terpolymer | 8.0 |
| 2-Amino-2-methyl-1-propanol | 0.6 |
| Water-dispersible silicone wax according to formula I (n = m = 16) | 0.5 |
| Perfume | 0.2 |
| n-Pentane | 8.0 |
| Dimethyl ether | 28.0 |
| Water | @ 100.0 |

An excellently well-setting hair spray is achieved having a homogeneous spraying pattern which does not produce any visible particle-shaped resin residues on the hair after application.

EXAMPLE 2

| | |
|---|---|
| Ethanol | 26.6 (% by wt.) |
| Acrylic acid/ethyl acrylate/N.-tert.-butyl acrylamide terpolymer | 5.0 |
| Vinyl pyrrolidone/vinyl acetate (30:70) copolymer (50% in isopropyl alcohol) | 6.0 |
| 2-Amino-2-methyl-1-propanol | 0.4 |
| Water-dispersible silicone wax according to formula I (n = m = 16) | 0.8 |
| Polyethylene glycol-(16)-dimethyl ether | 0.2 |
| Perfume | 0.2 |
| n-Pentane | 8.0 |
| Dimethyl ether | 28.0 |
| Water | @ 100.0 |

A hair spray is obtained with spraying properties complying with those of Example 1, and having additionally outstanding setting properties.

EXAMPLE 3

| | |
|---|---|
| Ethanol | 31.9 (% by wt.) |
| Acrylic acid/ethyl acrylate/N-tert.butyl acrylamide terpolymer | 5.0 |
| Vinyl pyrrolidone/vinyl acetate/vinyl propionate (30:40:30) terpolymer (50% in isopropanol) | 6.0 |
| 1-Amino-2-methyl-1-propanol | 0.4 |
| Water-dispersible silicone wax according to formula I (n = m = 16) | 0.5 |
| Polyethylene glycol-(16)-dimethyl ether | 0.1 |
| Perfume | 0.2 |
| n-Butane | 6.0 |
| Dimethyl ether | 30.0 |
| Water | @ 100.0 |

The spraying and setting properties of this hair spray essentially comply with the hair spray of Example 2.

We claim:

1. Hair spray composition having a low proportion of volatile compounds comprising (a) shout 5% to about 50% by wt. of at least one lower alcohol selected from the group of ethanol, n-propanol and isopropyl alcohol;

(b) about 15% to about 70% by wt. water;

(c) about 1% to about 15% by wt. of at least one film-forming polymer;

(d) about 0.1% to about 3% by wt. of water-dispersible silicone wax of the general formula I:

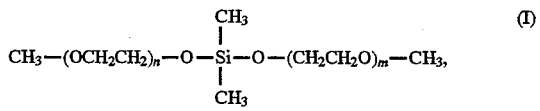

$$CH_3-(OCH_2CH_2)_n-O-\underset{\underset{CH_3}{|}}{\overset{\overset{CH_3}{|}}{Si}}-O-(CH_2CH_2O)_m-CH_3, \quad (I)$$

wherein n and m may be identical or different and denote an integer between 10 and 20, all percentages calculated to the total hair spray composition; said hair spray being packaged as one of e1) and e2), wherein e1) is an aerosol spray composition comprising as propellent a compound selected from the group consisting of dimethyl ether, dinitrogen oxide, compressed air, nitrogen and carbon dioxide, and e2) is a manually operated pump spray.

2. Hair spray according to claim 1, wherein the water-dispersible silicone wax is present in admixture with polyethylene glycol dimethyl ether in a weight proportion of 90:10 to 75:25.

3. Hair spray according to claim 1, comprising about 2.5% to about 10% by wt. of the film-forming polymer.

4. Hair spray according to claim 1, comprising as film-forming polymer at least one compound selected from the group consisting of anionic, amphoteric and nonionic polymer.

5. Hair spray according to claim 4, comprising as nonionic polymer a vinyl pyrrolidone homo- or copolymer.

6. Hair spray according to claim 4, comprising as amphoteric polymer a N-octyl (meth)acrylamide tertiary butyl aminoethyl methacrylate/acrylic acid terpolymer.

7. Hair spray according to claim 4, comprising as anionic polymer a crotonic acid copolymer.

8. Hair spray according to claim 4, comprising as anionic polymer an acrylic acid copolymer.

* * * * *